United States Patent [19]

Chervitz et al.

[11] Patent Number: 5,766,250
[45] Date of Patent: Jun. 16, 1998

[54] LIGAMENT FIXATOR FOR A LIGAMENT ANCHOR SYSTEM

[75] Inventors: Alan Chervitz; E. Marlowe Goble; Ramarao Gundlapalli, all of Logan, Utah

[73] Assignee: MedicineLodge, Inc., Logan, Utah

[21] Appl. No.: 736,554

[22] Filed: Oct. 28, 1996

[51] Int. Cl.$^6$ .................................................. A61F 2/08
[52] U.S. Cl. .................................................. 623/13; 606/72
[58] Field of Search .................................. 623/13, 11, 12; 606/72

[56] References Cited

U.S. PATENT DOCUMENTS

| | | |
|---|---|---|
| 4,744,793 | 5/1988 | Parr et al. |
| 4,772,286 | 9/1988 | Goble et al. |
| 4,784,126 | 11/1988 | Hourahane |
| 4,870,957 | 10/1989 | Goble et al. |
| 4,997,433 | 3/1991 | Goble et al. ............... 623/13 |
| 5,100,417 | 3/1992 | Cerier et al. |
| 5,129,902 | 7/1992 | Goble et al. |
| 5,152,790 | 10/1992 | Rosenberg et al. |
| 5,571,139 | 11/1996 | Jenkins, Jr. ............... 623/13 |

*Primary Examiner*—Debra S. Brittingham
*Attorney, Agent, or Firm*—M. Reid Russell

[57] ABSTRACT

A ligament fixator for a ligament anchor system and a process its use in an arthroscopic procedure for mounting a ligament graft end in a tunnel formed into a bone. The anchor system includes footing member for positioning in a bone tunnel, and includes a longitudinal opening formed therethrough, and a ligament carrying member that has a forward of proximal portion for fitting through the member longitudinal opening and includes a coupling for securing it to the footing member. The ligament carrying member further including as a rear or distal portion that incorporates a ligament mounting section having a center longitudinal axis wherefrom at least one and preferably a pair of spaced apart pointed posts extend at essentially right angles that include serrations or downwardly sloping teeth formed along at least one side of each post, the post or posts for passing through transverse holes formed in an end of a ligament graft, such as a bone end of a bone tendon ligament graft, with the ligament graft bone end urged onto the mounting plate posts axially mounting it thereto. The ligament carrying member with axially mounted ligament graft are guided in the bone tunnel and into the footing longitudinal opening, with the ligament carrying member to lock therein, completing the ligament graft end mounting in the bone tunnel. With, after the ligament graft is placed under tension and the opposite graft end secured, should an adjustment of ligament graft tension be desirable, the footing member is turned appropriately in the bone tunnel.

11 Claims, 4 Drawing Sheets

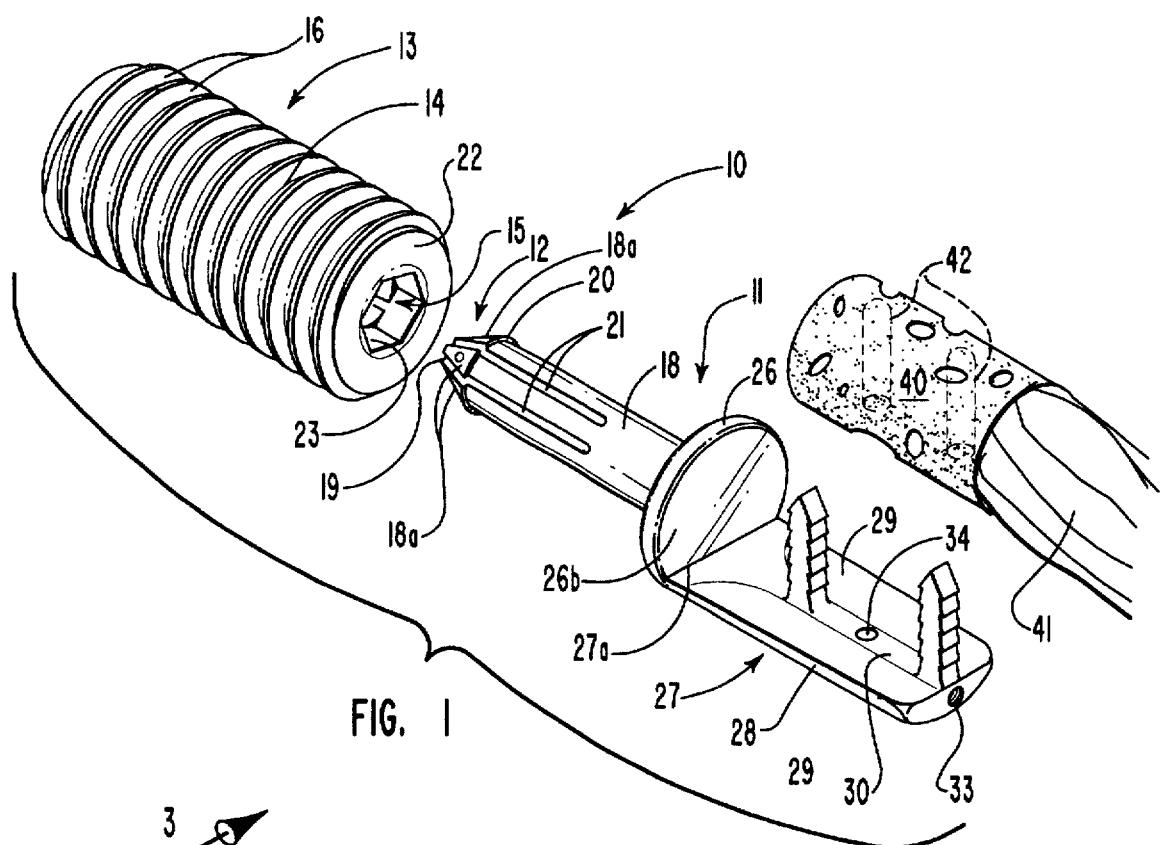
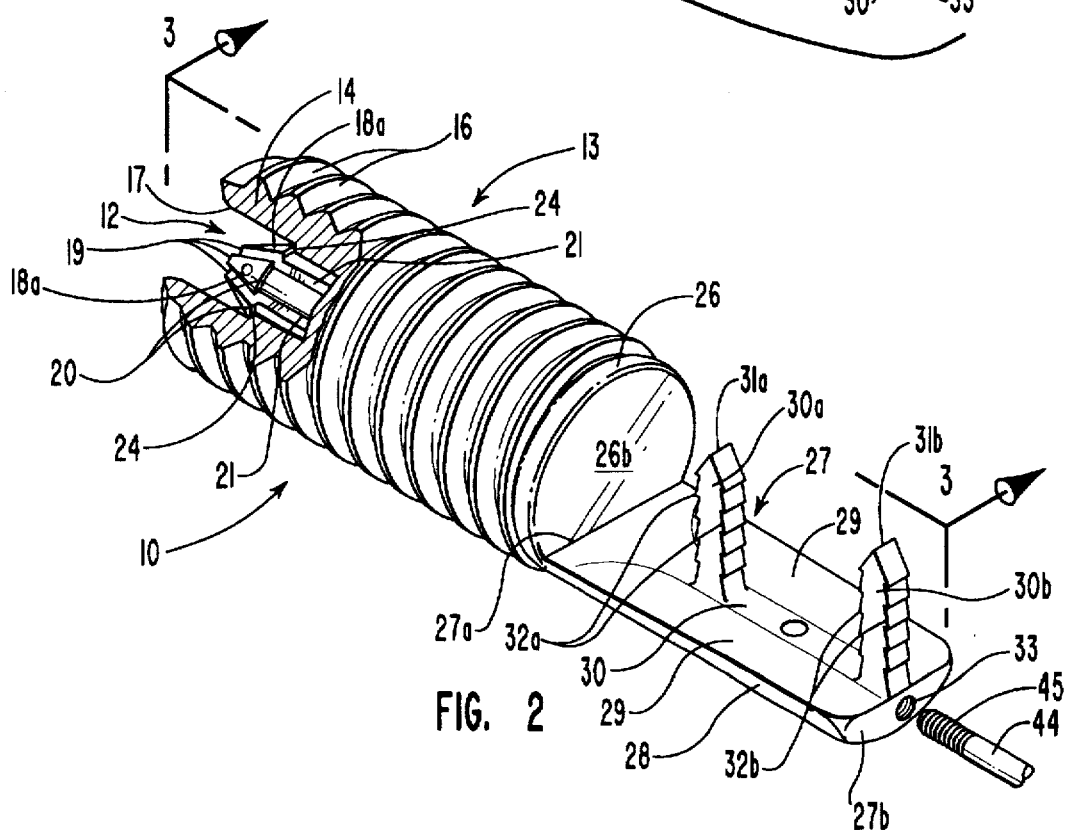

5,766,250

LIGAMENT FIXATOR FOR A LIGAMENT ANCHOR SYSTEM

BACKGROUND OF THE INVENTION

1. Field of the Invention

This invention relates to ligament anchor systems and devices for use in surgical procedures for the repair or replacement of a ligament and in particular to a male connector that incorporates a ligament mount or fixator for securing a ligament end thereto with the male connector for coupling into a female connector that has been seated in a bone tunnel, thereby mounting the ligament end in that bone tunnel.

2. Prior Art

In the discipline of arthoscopic surgery, for a ligament replacement procedure, a surgeon will form a tunnel into or through a bone that is to receive a ligament graft end maintained therein. For such ligament mounting, a ligament end has heretofore been connected, as by sewing it to a rear end of a male connector whose forward end is arranged for fitting into a female coupling that has been secured in the ligament tunnel. Which male and female connectors to join together, completing the endosteal mounting. An earlier U.S. Patent of one of the inventors, U.S. Pat. No. 4,870,957, shows an example of such arrangement that utilizes male and female connectors, with the female connector, like that preferred for the invention, having a threaded outer surface that is for turning into a prepared ligament tunnel. With the male connector, at its end opposite to its ligament mounting end, including a spring collet that is for fitting into a longitudinal opening formed through the female connector, exiting the female connector open end. In practice, with passage of the male member into the opening, the collet lip end will flex outwardly across an edge of the female connector opening proximal end, thereby locking the male to the female member. The present invention preferably utilizes this arrangement of male and female mounting members, and further provides a unique arrangement for securely mounting a ligament graft end to the male member.

Additional to the above cited earlier U.S. Patent of one of the inventors, U.S. Pat. No. 4,772,286, that is also set out in U.S. Pat. No. Re. 34,293, and U.S. Pat. No. 5,129,902, also show endosteal mounting arrangements that provide for connecting to, respectively, a natural or prosthetic ligament, or sutures, that connect to a ligament graft to one of the mountings. Such couplings of a ligament graft end or sutures to a connector, or connector element of these prior patents are, however, unlike the fixator arrangement of the present invention. Similarly, U.S. Pat. Nos. 4,744,793; 4,784,126; 5,100,417 and 5,152,790, show bone tunnel mountings that also provide for coupling to a ligament graft end, sutures or the like, but do not employ the particular ligament graft fixator arrangement of the present invention.

SUMMARY OF THE INVENTION

It is a principal object of the present invention to provide a bone anchor system for use for easily and reliably securing an end of a biological or prosthetic ligament graft, or ligament type device, onto a distal end of male member or component of a bone tunnel mounting used in a ligament repair or replacement procedure.

Another object of the present invention is to provide a bone anchor system that is suitable for use in a process for endosteally mounting a ligament end in a prepared ligament tunnel in an arthroscopy surgical procedures.

Another object of the present invention is to provide a bone anchor system where a ligament graft end, such as a bone end of a bone tendon bone ligament graft, can be quickly and reliably mounted to a mounting end of a male connector member that is arranged for fitting into, so as to lock to, a female footing mounted in a prepared ligament tunnel, which male member locking is provided by a spring collet formed on a proximal end thereof that, through a longitudinal opening in the seated female footing, a lip of the male member spring collet end will flex outwardly to pass over the edge of the female footing opening, securely locking to prevent withdrawal of the male member back through the female footing.

Another object of the present invention is to provide a bone anchor system that includes, as a fixator for securing a ligament end onto a distal portion of the male member, a flat longitudinal distal end section of the male member that includes at least one, and preferably a pair of parallel posts, that extend at right angles from the flat surface, are each pointed and each preferably includes at least one side formed with serrations or teeth therealong, the post or posts for passing through an end of a ligament graft, skewering it onto the male member distal end.

Another object of the present invention is to provide a bone anchor system that is easily installed in a practice of an arthroscopic surgical procedure to repair or replace a ligament, for example, a procedure that is practiced on a patient's knee for replacing a cruciate ligament, utilizing a threaded female footing that is first turned into a prepared ligament tunnel and a male member, that includes a spring collet proximal end, has a ligament mounting plate with posts formed in a distal portion thereof and includes a ligament graft end skewered onto which posts.

Still another object of the present invention is to provide a process for endosteally mounting a ligament graft end in a prepared ligament tunnel utilizing the footing and male member where the male member proximal end is to fit into the open threaded footing end, and is passed therealong to where the male member spring collet end exits the footing such that a base edge or lip of the spring collet end will flex outwardly over the footing opening edge, locking the members together, completing an endosteal mounting.

Still another object of the process of the present invention is to provide for ligament graft tensioning by attaching the opposite ligament graft end to the bone cortex surface, adjacent to the tunnel entrance, as with a staple, or the like, or with the ligament graft under tension fitting a tool to the footing and turning it into or out of the tunnel section increasing or decreasing tension.

Still another object of the present invention is to provide a bone anchor system, that may be a biodegradable system, for mounting a ligament graft, or ligament type device, within a prepared ligament tunnel.

The present invention is in a ligament fixator for a bone anchor system that includes a threaded cylindrical member that is open longitudinally therethrough and is preferably threaded along its outer surface for turning to bind in the wall of a prepared ligament tunnel; and a male member that includes a spring collet forward or proximal end that is for fitting into to pass through the threaded member longitudinal opening, such that a spring collet outer lip will flex over the edge of the threaded member opening, thereby prohibiting the male member from being pulled back through the footing. The male member includes, as a distal section, a flattened ligament mounting plate wherefrom one, and preferably a pair, of spaced posts, are mounted, each to extend at right angles therefrom. The posts are each pointed at their ends and preferably include, along at least one side of each, and preferably along two opposite sides of each, serrations, teeth, or the like, that are for receiving an end of a ligament graft skewered thereon. The ligament graft end, that is preferably a bone end of a bone tendon bone ligament graft, or the like, preferably will have been drilled appropriately, to fit onto the post or posts, extending axially from the male member distal end.

For installation, the male member with the ligament graft mounted axially thereto has its proximal spring collet end pulled or fitted through an open end of the bone tunnel to travel therealong into the threaded footing longitudinal cavity. The male member spring collet end preferably has a cone shaped end that is separated into four equal segments by crossing slots that extend longitudinally into a cylindrical portion thereof. The cone base has an edge that is larger in diameter than the diameter of the threaded footing longitudinal opening. The four spring collet segments in the male member end form arcuate segments, that, when passed into the longitudinal opening, will be compressed together and remain so during travel through the threaded footing opening. The spring collet segments flex outwardly at the tunnel end, with the edge of the each segment base undersurface to travel over the opening edge, prohibiting withdrawal of the male member. Whereafter, the opposite ligament graft end can be placed in tension and connected, as by stapling, to a bone cortex surface that is adjacent to a bone tunnel end, completing the ligament mounting. Which ligament tension can be later adjusted by fitting an appropriate tool through an arthroscopic port to engage the foot and turn it in the tunnel section to increase or decrease ligament tensioning.

In practice, utilizing a driver, the threaded footing is turned into the bone tunnel to an appropriate distance from an open bone tunnel end. A selected length of ligament graft or ligament type device is secured, as by skewing the end thereof onto the post or posts that extend at right angles outwardly from the transverse male member ligament mounting plate. For which ligament end mounting holes can be formed into or through the ligament graft end, as by drilling an end of a bone tendon bone ligament graft, which holes are then positioned over the pointed ends of the posts to be forced thereon. The ligament graft end is thereby mounted to the male member to extend axially from the male member distal end. The ligament graft can be held by a surgeon operator who, using a driver, that is releasably connected to the male member, or by pulling a line that is connected to extend axially from the male member spring collet end, urges the male member along the tunnel so as to fit the spring collet end into the threaded footing to travel therealong to the footing proximal end. Thereat, the spring collet end cone base edge flexes outwardly over the edge of the threaded footing opening, locking the threaded footing and male member together so as to endosteally mount the ligament graft end in the bone tunnel.

As desired, to release or adjust tension on the ligament graft, a small incision can be made into the knee, to expose an end of the ligament tunnel wherein the threaded footing is turned, allowing access to the male member spring collet end of the footing end. The spring collet end, can be released, as by squeezing the spring collet segments together, allowing back passage through the female member opening, releasing the male member or the ligament tensioning can be adjusted by fitting a turning tool to the footing and turning it appropriately in the ligament tunnel.

BRIEF DESCRIPTION OF THE DRAWINGS

These and other objects and features of the present invention will become more apparent from the following description in which the invention is described in detail in conjunction with the accompanying drawings.

FIG. 1 is a profile perspective view of a threaded footing with a male member proximal end portion shown cross cut to form a spring collet and is aligned for fitting into a longitudinal opening formed through a female member threaded footing, and showing the male member as including a center disk that has a like diameter to that of the footing and wherefrom a distal section extends rearwardly as an arcuate segment with a flat surface wherefrom a pair of spaced posts extend at right angles upwardly, and showing a bone of a bone tendon ligament graft positioned for skewering onto the posts;

FIG. 2 is a view like that of FIG. 1 with the male member shown as having been fitted into the female threaded footing and showing, through a broken away section, a base edge of the cone shaped spring collet proximal end as having flexed over the edge of the longitudinal opening in the female member footing proximal end, and showing a threaded end of a rod type insertion tool aligned for turning into a threaded hole in the male member distal end;

DETAILED DESCRIPTION

Figure 3A:
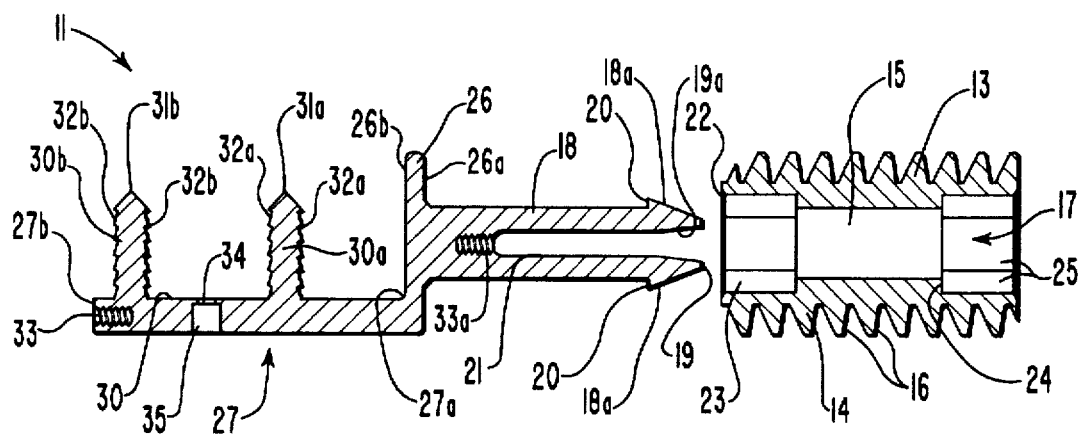
FIG. 3A is a side elevation sectional view taken along the line 3—3 of FIG. 2, showing the male member aligned for fitting into the female member threaded footing longitudinal opening.
Figure 3B:
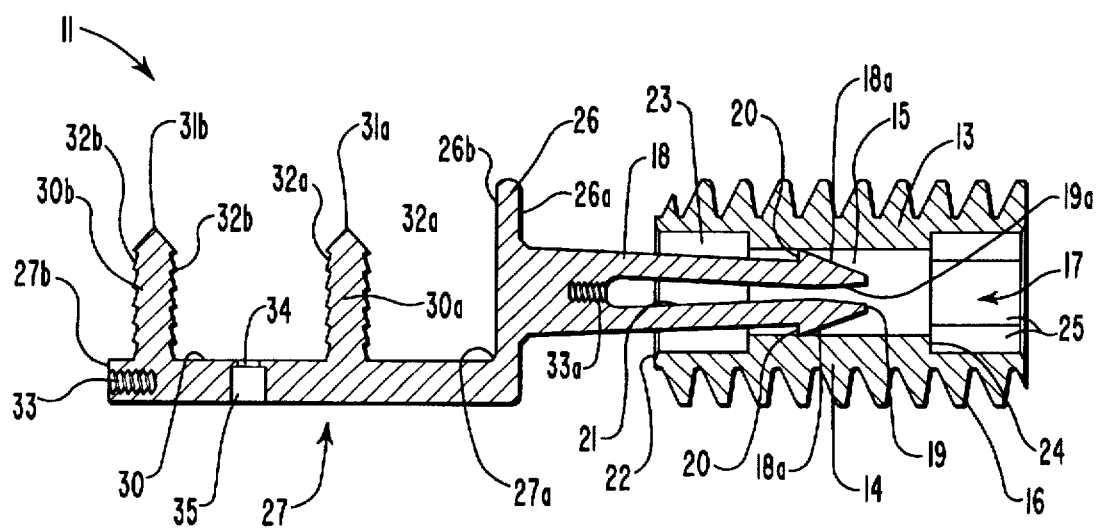
FIG. 3B is a view like that of FIG. 3A showing the spring collet end of the male member as having traveled into the female member threaded footing longitudinal opening.
Figure 3C:
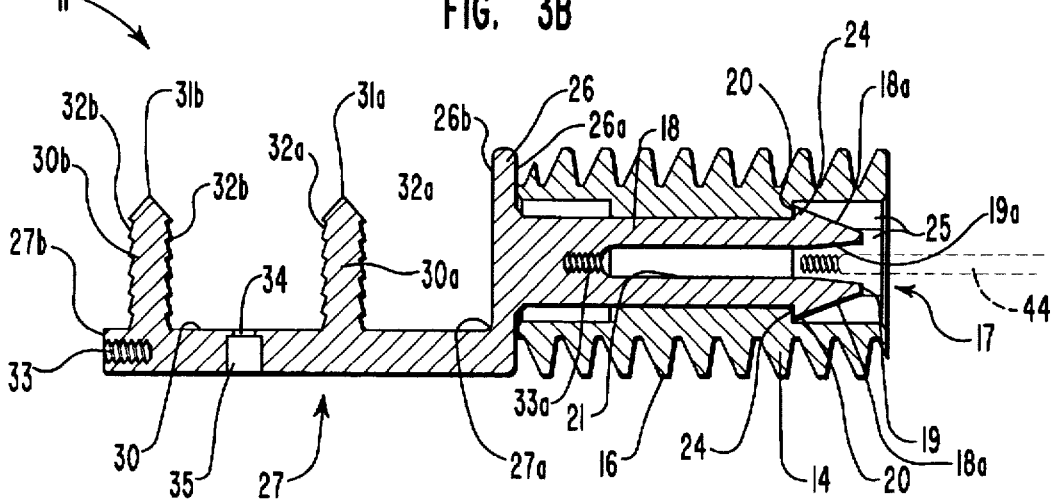
FIG. 3C is a view like that of FIGS. 3A and 3B showing the male member cone shaped spring collet end as having traveled into an outwardly stepped proximal end portion cavity of the female member threaded footing longitudinal opening, with a cone base edge of the spring collet end shown as having flexed over an edge of a step formed in the female member distal end, locking the male member and footing together.

FIG. 1 shows a profile perspective view of a ligament anchor system 10 of the invention that includes a male member 11 that is shown as having a cross-cut across a forward or proximal end 12 aligned for fitting into a center longitudinal passage 15 formed in a cylindrical body 14 of a female member threaded footing 13, hereinafter referred to as threaded footing 13. The threaded footing 13 is externally threaded at 16, along its length. The threads 16 are deep for providing a strong purchase in a bone wall of a tunnel 50, to resist withdrawal. Appropriate threads for this use as shown and described in the cited U.S. Pat. No. 4,870,957 of one of the present inventors. FIG. 2 shows the male member 11 as including a proximal portion 18 that is preferably like that of the '957 patent, and includes the cross-cut end 12 that is shown as a cone 19 that has been cross-cut from its apex, forming a spring collet, that has been fitted into the center longitudinal passage 15 of the threaded footing 13, as shown in FIGS. 3A and 3B. The cross-cut end 12, is shown in FIG. 3C, as having passed into an outwardly stepped proximal cavity 17 formed in a proximal end portion of the center longitudinal passage 15, locking therein.

FIG. 2 shows the male member 11 as including a cylindrical forward or proximal portion 18 with the cross-cut end 12 that is preferably a cone shaped tip 19 that is formed into the spring collet by longitudinal slots 21 cut from the cone apex through the cone base, which slots are at right angles to one another, to form a cross dividing the proximal portion into four like segments 18a. The slots 21 to extend longitudinally from the cone 19 apex to form the proximal segments 18a, as shown best in FIGS. 3A through 3C. The cone shaped tip 19 preferably includes a base with an edge 20 that is at approximately a right angle to the proximal portion 18 longitudinal axis. The crossed slots 21 segment the cone into the equal proximal segments 18a. So arranged, the cross-cut cone shaped tip 19 functions as the spring collet, with the proximal segments 18a, that are quarter segments, collapsing together, as shown in FIG. 3B, when the cross-cut end 12 is urged into a distal end of the center longitudinal passage 15 of the threaded footing 13.

Figure 4:
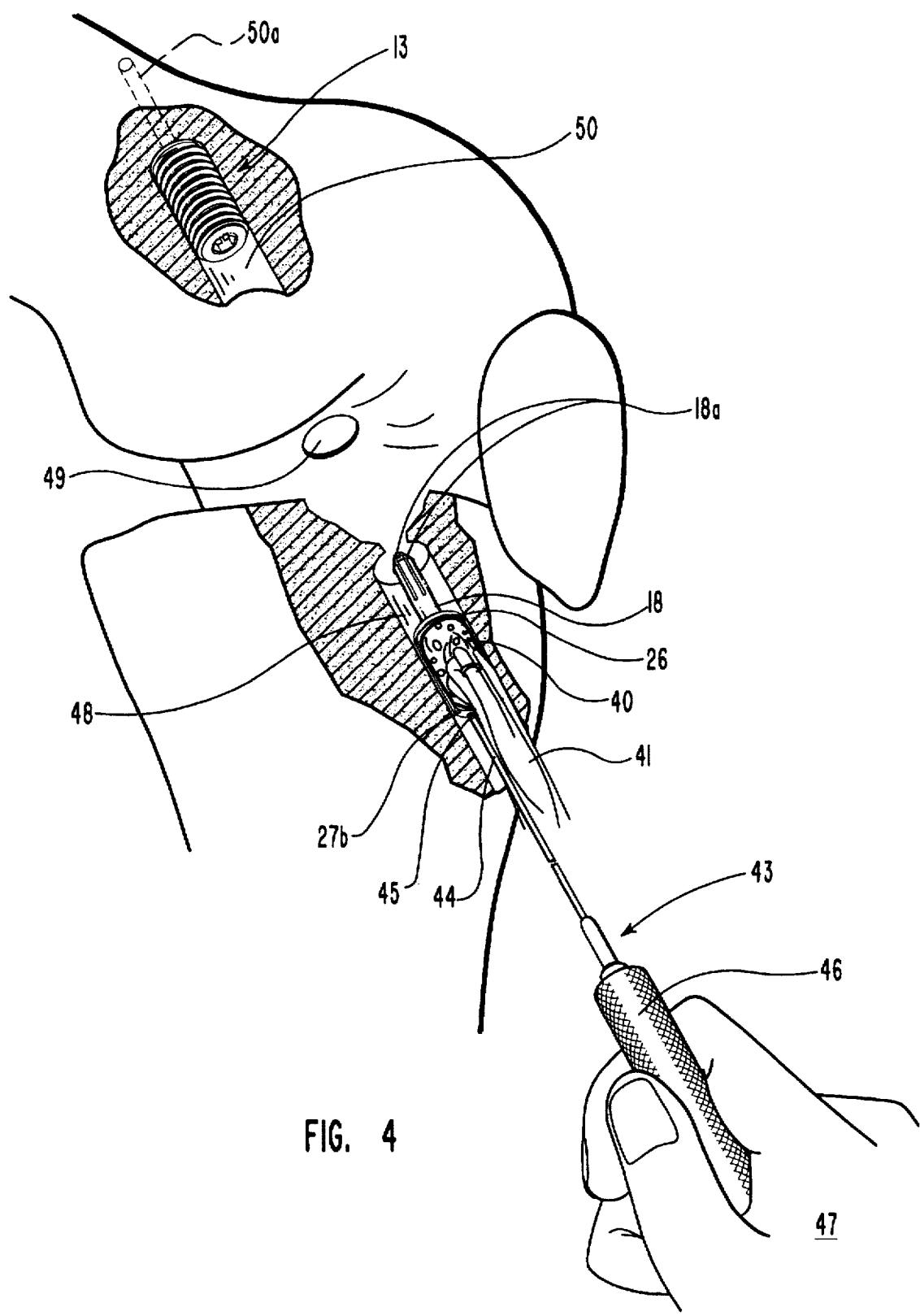
FIG. 4 is a profile perspective view showing a patient's knee, and showing a straight tunnel as having been formed through the proximal tibia, across the interarticular joint and into the distal femur, as a first tunnel section, wherefrom a lesser diameter second tunnel section is shown in broken lines extending therefrom and exiting the bone cortex, with a threaded footing shown as having been turned into the femoral tunnel section and showing a surgeon/operator's hand holding a handle end of an insertion tool having a straight narrow blade whose end is turned into a threaded hole formed in a male member distal end, with a bone end of a bone tendon ligament graft shown extending axially from the male member distal end.
Figure 5:
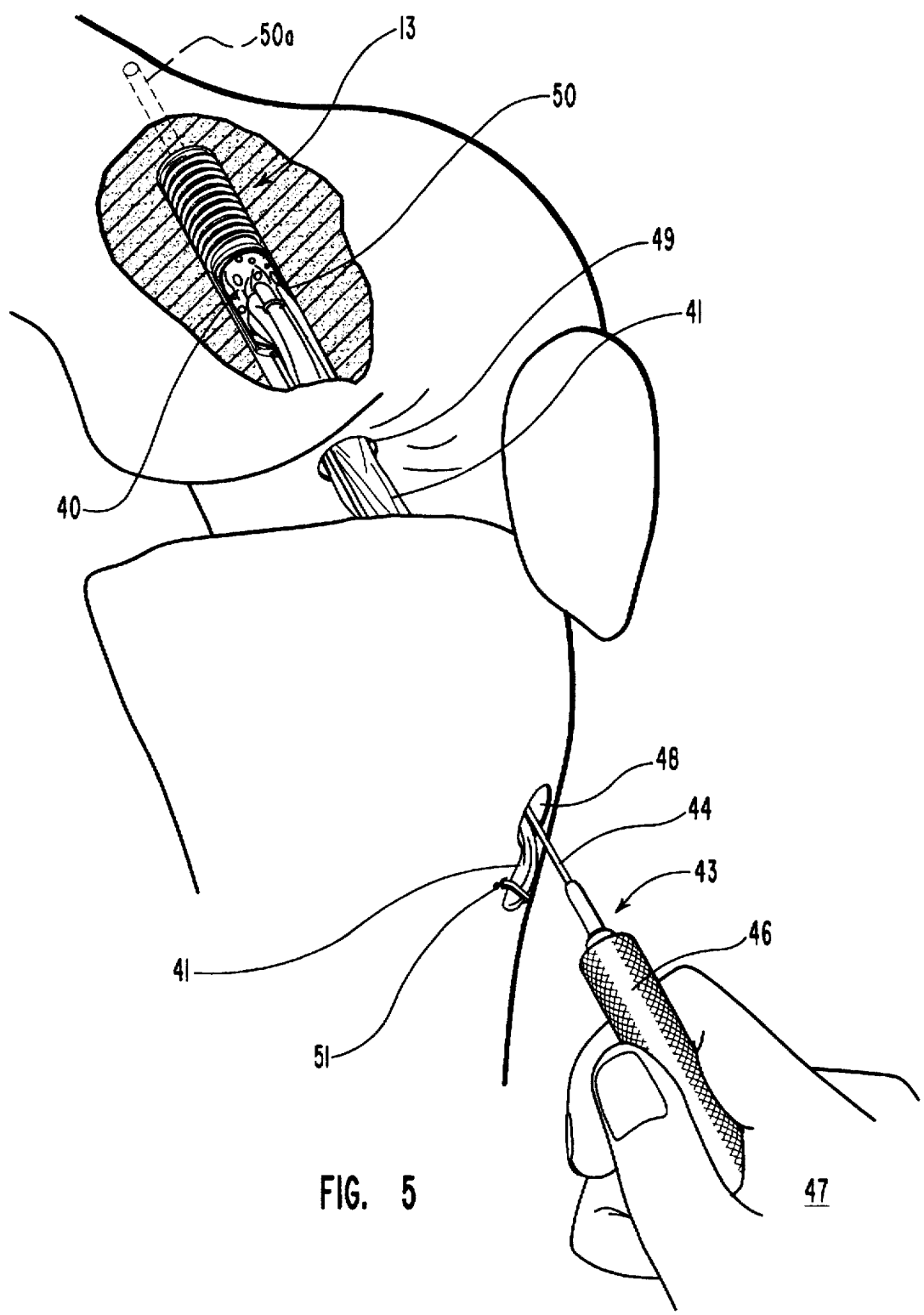
FIG. 5 is a view like that of FIG. 4, only showing the male member as having passed into the femoral tunnel section and into the threaded footing longitudinal opening to lock therein, as shown in FIG. 3C.

The threaded footing 13 distal end 22 may be formed with a sided opening 25, not shown, as shown best in FIG. 1, that preferably has a hexagon cross section, to accommodate a turning tool, passed through a femoral second tunnel section, shown in broken lines in FIG. 4, for turning the threaded footing to a distal end of a first femoral tunnel section 50, placing it therein as shown in FIGS. 4 and 5, though other number of sides greater or less than six sides could be so utilized, depending upon the configuration of the turning tool, within the scope of this disclosure. Which turning tool such as an alan wrench, can be fitted into the sided opening 25 after installation for readjusting ligament graft tensioning. Further, as shown best in FIG. 3B, the opening 23 sides contact the surfaces of the cone shaped tip 19 proximal segments 18a, to initially flex them inwardly in anticipation of the of the tip passage into the center longitudinal passage 15. In which passage, the cone shaped tip 19 proximal segments are further flexed together as they pass along that passage 15. At the proximal end of the threaded footing the center longitudinal passage 15, a cavity 17 is formed that is the interior of the sided opening 25 to have a greater diameter than that of the center longitudinal passage 15. The longitudinal passage 15, at its junction to sided opening 25, is thereby stepped outwardly into a flat step 24 that is to receive the surface of base or skirt edge 20 of the cone shaped tip 19 proximal segments 18a, flexed thereover. Which flexure occurs as the proximal segments 18a, flex outwardly when the cone base or edge 20 travels beyond the center longitudinal passage 15 proximal end, as shown in FIG. 3C. Preferably, the proximal cavity 17, as set out above, is sided, to receive the turning tool fitted therein, and to later receive the turning tool for adjusting ligament tensioning, as required, though, of course, it need not be sided within the scope of this disclosure. Such turning tool, such as an alan wrench, not shown, can therefore be fitted at open proximal tunnel cortex end, shown in broken lines at 50a in FIG. 5, after cone shaped tip 19 is compressed or cut away the male member 11 to provide for turning of the threaded footing 13 back into or out of the tunnel, as set out and described below with respect to a demounting of a ligament graft for adjusting the tension thereof.

The male member 11, additional to the described proximal portion 18, and proximal segments 18a, includes a disk 26 that is arranged as a male member mid portion and to a forward face 26a of which disk the male member proximal portion including the four proximal portions 18 with proximal segments 18a, axially mounted to extend outwardly and at approximately a right angle from the center thereof. A ligament mounting plate 27 is secured at an end 27a to extend, at approximately a right angle from a lower section along an edge section of a distal face 26b of the disk 26. The mounting plate 27 is curved around an undersurface 28 and has an upper face 29 that is essentially flat but may slope slightly upwardly from opposite edges into a flat center portion 30 forming a cradle, within the scope of this disclosure. A pair of spaced aligned posts 30a and 30b are both shown extending at approximately right angles upwardly from the flat center portion 30 and are each formed to have a rectangular cross section. The posts 30a and 30b are pointed at their top ends 31a and 31b, respectively, and are preferably serrated or have downwardly slopping teeth 32a and 32b formed along their opposing sides. The posts 30a and 30b, as shown in FIG. 1, are to fit into transverse holes 42, shown in broken lines, that have been formed across a bone end 40 of a ligament graft 41. So arranged, an operator, not shown, fits the bone end 40 transverse holes 42 onto the post pointed ends 31a and 31b, and pushes on the side of the bone end 40 to pass or skewer the posts 30a and 30b through the transverse holes, thereby mounting the bone end to the upper face, as shown in broken lines. The bone end 40 is thereby axially connected to the male member for fitting, as shown in FIGS. 4 and 5, into a ligament tunnel, as set out and described below. While two spaced posts 30a and 30b are shown, it should be understood that only one such post is required within the scope of this disclosure, and that such post need not have a serrated or toothed side and that more than one such serrated of outwardly sloping toothed side could be so employed within the scope of this disclosure.

For inserting the male member 11, as shown in FIGS. 4 and 5, the mounting plate 27 distal end 27b preferably has a threaded hole 33 formed longitudinally therein that is for receiving a threaded end 45 of a straight shaft 44 of an insertion tool 43, shown in FIGS. 2, 4 and 5. After the bone end 40 is skewered onto the posts 30a and 30b, as shown in broken lines in FIG. 1, a pin or tool end, not shown, can be fitted through a hole 35 formed from the curved undersurface 28, through the mounting plate 27, as shown in FIGS. 3A, 3B and 3C. Such pin or tool end, not shown, would travel out of a top end 34 of hole 35 and contact the surface of the bone end 40 for aligning the bone end 40 onto the posts 30a and 30b, or to reset the bone end, the pin or tool end could be used to push the bone end off of the posts 30a and 30b. Such bone end 40 removal would be opposed by the serrated or slopping teeth 32a and 32b.

FIGS. 4 and 5 shown a surgeon/operators hand 47 holding a handle end 46 of the insertion tool whose threaded end 45 of shaft 44 has been turned into the threaded hole 33 that has been formed into the mounting plate 27 distal end 27b. The threaded member 13 is turned, as shown in FIG. 4, into a femoral tunnel section 50, utilizing a sided end of a turning tool, such as an alan wrench, not shown, that has been fitted into the sided opening 23 formed in the threaded member 13 distal end or inserted through the tibial tunnel section 48 or through the femoral tunnel section 50a, fitting into cavity 17. The surgeon/operator can then guide the male member 11 proximal portion 18 through a tibial cortex end of a tibial tunnel section 48 to pass through the interarticular joint and into the femoral tunnel end 49 and fit into the distal end of the threaded footing 13 center longitudinal passage. Alternatively, as shown in FIGS. 3A, 3B and 3C, a threaded hole 33a is formed in a distal end of proximal cavity 17 to receive the threaded end 45 of shaft 44 turned therein after passage from the second and first femoral tunnel sections 50a and 50, and through the tibial tunnel section 48, to draw the male member 11 into the first femoral tunnel section 50. In this arrangement, with the male member proximal portions 18 squeezed together if the passage made by the intersection of the cross cuts into the cone shaped tip is not large enough to allow the proximal segments 18a, to close together, as shown in FIG. 3B, hole 19a can be drilled into the proximal end of the cone shaped tip 19 at the intersection of the cross cuts. The hole 19a walls are thereby formed to allow the proximal 18s to squeeze together, as shown in FIG. 3B, with the shaft 44 fitted therethrough, as shown in FIG. 34 and discussed above. Alternatively, a cable or suture can be used to pull the male member 11 into the threaded footing 13, eliminating a need for forming hole 19a, within the scope of this disclosure.

In practice, the male member proximal portions 18 travel into the threaded footing 13, as shown in FIGS. 3A and 3B, to the seated attitude as shown in FIG. 3C and in FIG. 5. This completes the ligament graft end 40 endosteal mounting in the femoral tunnel section 50. The ligament graft 41 can be placed under tension, with an end thereof that extends from the tibial tunnel section cortex end to be fixed to the cortex surface as by hammering a staple 51 that straddles the ligament graft end into the bone cortex, as shown in FIG. 5. The insertion tool 43 can be removed as by turning the threaded end 45 of the shaft 44 out of the threaded hole 33 or threaded hole 33a, or by releasing the suture or cable from the male member proximal end, the insertion tool suture or cable can then be pulled out through the tibial tunnel section 48 or the femoral second tunnel section 50a.

Further, after initially setting ligament graft tension, should an adjustment to that tensioning be needed or advisable, a surgeon/operator can refit the turning tool, not shown, through the cortex end of tunnel section 50a to pass into and engage the footing opening 17 sides 25, for turning the footing into or out of the tunnel section, thereby adjusting ligament graft tension.

Shown best in FIGS. 3A, 3B and 3C, in a passage of the proximal portion 18 proximal segments 18a, through the threaded footing 13 center longitudinal passage 15, the cone shaped tip 19 proximal sections are initially flexed or collapsed towards one another as they travel through the passage and, at the passage stepped end portion 17, the cone base edge 20 passes over the step surface 24, prohibiting withdrawal. To release this coupling, a surgeon/operator can form a tunnel to intersect the femoral tunnel closed end, above the threaded footing proximal end, and can then, utilizing an appropriate tool, to collapse together the cone tip 19 and proximal sections 18a, together, allowing the proximal portion 18 to slide back along the threaded footing 13 longitudinal passage 15, releasing the ligament graft end femoral tunnel section endosteal mounting.

In practice, a threaded footing 13 and male member 11 can be fabricated from an surgically acceptable material including a metal such as titanium, or, within the scope of this disclosure, a resilient plastic material, shown in the removed section of FIG. 1, such as Delrin™, can be used for both the threaded footing 13 and the male member 11 to provide, as required, a biodegradable ligament mounting for the bone tendon ligament graft, as shown, or for other ligament graft, within the scope of this invention.

While a preferred embodiment of the present invention in a ligament mounting for a ligament fixator for a ligament anchor system and its use have been shown and described herein, it should be apparent that the present disclosure is made by way of example only and that variations thereto are possible within the scope of the disclosure without departing from the subject matter coming with the scope of the following claims and a reasonable equivalency thereof, which claims we regard as our invention.

We claim:

1. A ligament fixator for a ligament anchor system comprising, a footing means that includes a bone engaging outer surface for fixing in a bone tunnel and includes a longitudinal passage therethrough; a ligament carrying member means that includes, on a proximal end a straight cylindrical section that has a cone shaped proximal end, as a means for connecting said ligament carrying member means to said footing means, which said cone shaped proximal end includes a base having a lesser diameter than that of said footing means longitudinal passage and is slotted longitudinally to form a spring collect, ligament graft mounting means arranged on said ligament carrying member distal end that includes post means for insertion into a section of a ligament graft whereby said ligament graft will extend axially from said mounting means, and said mounting means includes a central portion having forward and rear faces with an essentially flat section extending, at approximately a right angle from said central portion forward face, which said essentially flat section includes said post means extending upwardly therefrom; and including means for guiding said ligament carrying member cone shaped proximal end into said footing means longitudinal passage.

2. A ligament fixator for a ligament anchor system as recited in claim 1, wherein at least one end of the footing means longitudinal passage is stepped outwardly to form an interior shelf that is at a right angle to the longitudinal axis of said longitudinal opening and is to receiving an edge of the ligament carrying member means cone base that will flex thereover when said cone shaped proximal end has passed into said longitudinal opening stepped section.

3. A ligament fixator for a ligament anchor system as recited in claim 1, wherein the footing means includes flat proximal and distal faces, and the longitudinal opening adjacent to both said faces is walled for receiving an end of a driver shaft fitted therein as the means for turning said footing means into or out or a bone tunnel.

4. A ligament fixator for a ligament anchor system as recited in claim 1, wherein the footing means is formed from a biodegradable material.

5. A ligament mounting for a ligament anchor system as recited in claim 1, wherein the footing means and the ligament carrying member are both formed from a biodegradable material.

6. A ligament mounting for a ligament anchor system as recited in claim 1, wherein the ligament carrying member central portion is disk shaped, has flat essentially parallel front and rear faces and is approximately a same diameter as a cross section of the footing means; and the ligament graft end mounting means extends from an arcuate edge section of said disk shaped central portion rear face and the essentially flat section includes at least one post as the post means that extends outwardly from a location along a center longitudinal axis of said flat section, and said single post is pointed at its end and is serrated or has downwardly sloping teeth formed along at least one post side.

7. A ligament mounting for a ligament anchor system as recited in claim 6, wherein the ligament carrying member graft end mounting means essentially flat section includes a pair of posts as the post means with each said post including serrations or downwardly slopping teeth formed along post sides that are on each parallel and extend from points along the longitudinal axis of said essentially flat surface.

8. A ligament mounting for a ligament anchor system as recited in claim 7, further including a hole formed through the graft end mounting means essentially flat section between the posts.

9. A ligament mounting for a ligament anchor system as recited in claim 1, further including a longitudinal hole formed in the rear or distal end of the ligament carrying member means as the means for guiding that is arranged to receive and releasable connect to an end of an insertion tool fitted therein.

10. A ligament mounting for a ligament anchor system as recited in claim 1, further including a longitudinal hole formed through the center of the ligament carrying member straight cylindrical section cone shaped proximal end and into an end of the slot which said longitudinal hole is arranged to receive and releasable connect to an end of an insertion tool means fitted therein for pulling said ligament carrying member straight cylindrical section into the footing means.

11. A ligament fixator for a ligament anchor system comprising, a footing means with a bone engaging outer surface for fixing in a bone tunnel; a ligament carrying member means that includes, on a proximal end, means for connection to said footing means; ligament graft end mounting means arranged as a distal end of said ligament carrying member that includes post means for insertion into a ligament graft, for axially connecting said ligament graft onto said mounting means; and means for turning said footing means within said tunnel section for adjusting ligament tension that includes forming walls in at least one end of a longitudinal passage formed through said footing means opposite to the footing means end that receives said ligament carrying member means fitted therein, which said walls are for receiving an end of a tool fitted therein for turning said footing means.

* * * * *